(12) United States Patent
Guthermann (10) Patent No.: US 6,442,411 B1
(45) Date of Patent: Aug. 27, 2002

(54) METHOD FOR IMPROVING CALIBRATION OF AN INSTRUMENT FOR NON-INVASIVELY MEASURING CONSTITUENTS IN ARTERIAL BLOOD

(75) Inventor: Howard E. Guthermann, Newton, MA (US)

(73) Assignee: Optix, LP, Jupiter Island, FL (US)

( * ) Notice: Subject to any disclaimer, the term of this patent is extended or adjusted under 35 U.S.C. 154(b) by 0 days.

(21) Appl. No.: 09/552,332

(22) Filed: Apr. 19, 2000

Related U.S. Application Data (60) Provisional application No. 60/130,536, filed on Apr. 21, 1999.

(51) Int. Cl.[7] .................................................. A61B 5/00
(52) U.S. Cl. ........................ 600/322; 600/336; 600/310
(58) Field of Search ................. 600/309–311, 315–316, 600/322–324, 326, 328, 330, 336; 356/39–42

(56) References Cited

U.S. PATENT DOCUMENTS

| | | | |
|---|---|---|---|
| 4,805,623 A | | 2/1989 | Jobsis |
| 4,834,532 A | * | 5/1989 | Yount ........................... 356/41 |
| 5,137,023 A | | 8/1992 | Mendelson et al. |
| 5,148,022 A | | 9/1992 | Kawaguchi et al. ........ 250/341 |
| 5,179,951 A | | 1/1993 | Knudson |
| 5,227,986 A | | 7/1993 | Yokota et al. .............. 364/571 |
| 5,297,548 A | | 3/1994 | Pologe |
| 5,337,745 A | | 8/1994 | Benaron |
| 5,377,674 A | | 1/1995 | Kuestner |
| 5,424,545 A | | 6/1995 | Block et al. ................ 250/343 |
| 5,434,412 A | | 7/1995 | Sodickson et al. .......... 250/343 |
| 5,507,288 A | * | 4/1996 | Bocker et al. ............... 600/322 |
| 5,553,615 A | | 9/1996 | Carim et al. |
| 5,672,875 A | | 9/1997 | Block et al. ................. 250/343 |
| 5,692,503 A | * | 12/1997 | Kuenstner .................... 600/322 |
| 5,743,262 A | * | 4/1998 | Lepper, Jr et al. .......... 600/316 |
| 5,755,226 A | * | 5/1998 | Calim et al. ................. 600/323 |
| 5,823,966 A | | 10/1998 | Buchert ...................... 600/473 |
| 5,836,317 A | | 11/1998 | Kunst | |

FOREIGN PATENT DOCUMENTS

| | | |
|---|---|---|
| WO | WO 9732521 | 9/1997 |

* cited by examiner

*Primary Examiner*—Eric F. Winakur
*Assistant Examiner*—Matthew Kremer
(74) *Attorney, Agent, or Firm*—Lahive & Cockfield, LLP (57) ABSTRACT

The absence of a defined optical pathlength for in vivo measurements creates problems for the noninvasive measurement of analyte concentration. These problems can be reduced by combining measurements made at several wavelengths and using the fact that normal renal function causes the concentration of water in whole blood to be tightly controlled. Hence, the concentration of water in arterial blood can serve as a useful internal standard for such measurements. The measurements are then procured so as to remove the dependency of concentration on path length traversed by the illuminating radiation and on the scattering properties of the volume through which the illuminating radiation propagates. Using this method, one can create improved calibration for measurements of absorbing constituents in arterial blood and thereby provide absolute concentration measurements of constituents such as hemoglobin and glucose in arterial blood.

12 Claims, 4 Drawing Sheets

METHOD FOR IMPROVING CALIBRATION OF AN INSTRUMENT FOR NON-INVASIVELY MEASURING CONSTITUENTS IN ARTERIAL BLOOD

This application claims the benefit of U.S. Provisional Application No. 60/130,536, filed Apr. 21, 1999.

BACKGROUND OF THE INVENTION

The present invention relates to the detection and measurement of the concentration of constituents of a solution or suspension using radiation, preferably near-infrared radiation. More particularly, methods have been developed for the noninvasive measurement of the concentration of constituents such as hemoglobin and its variants and derivatives, glucose, cholesterol and its combined forms, drugs of abuse, and other analytes of clinical and diagnostic significance. Because these methods do not require the withdrawal of blood in order to perform these measurements, they are particularly suitable for home testing of glucose levels in diabetics and of urea or creatinine levels in patients undergoing home dialysis. The present invention provides a method of calibrating these measurements to obtain an absolute concentration without the requirement of obtaining extensive calibration data for each subject.

In addition to home testing, development of noninvasive clinical testing procedures has become an important goal, due to the widespread fear of AIDS and other diseases, such as hepatitis, which can be spread through the use of invasive procedures.

In the published research, a major issue in the in vivo quantification of blood analyte concentrations is the problem of how to take the signals generated by the apparatus and create from those signals an absolute value for the constituent concentration of interest. Current methods for the evaluation of concentration levels involve conversion of the signals to an estimated constituent concentration by some arbitrary algorithm using values generated by a contemporaneous set of invasive measurements from appropriately generated samples of blood or tissue. If the concentrations estimated by the converted signals and the concentrations estimated by the invasive measurements are highly correlated, then the correlation thus found is accepted as a "calibration curve" for the constituent of interest. However, the calibration curve thus generated is not necessarily valid over a wider range of subjects or physiological conditions than the range used to generate the curve.

In cases where only a relative trend in the data is of interest an accurate calibration is less critical and the foregoing method is adequate. However, in many cases, either calibration data are unavailable or a more accurate estimate of the constituent concentration is required. For these cases, a calibration method applicable to all subjects under all conditions is desirable.

A number of related publications suggest the use of water as an internal standard. Since water is an absorber in the near infra-red, the general approach is to measure the optical effect of water and to compare it with the optical activity of the constituent of interest. For example, Matcher et al. (Phys. Med. Biol., 38, 177, 1993) discusses the use of certain features of the water absorption spectrum to estimate the "differential path length" traveled by radiation in a scattering medium which includes water. However, their calculation for the concentration of water in the tissue studied (the human forearm) varies by approximately 12% around the mean value. Other publications (Documenta Geigy, $7^{th}$ edition, 1970) indicate that, depending on the tissue of interest, water concentrations can vary between 60% and 90%.

Jobsis (U.S. Pat. No. 4,805,623) describes a method in which an unknown concentration is estimated using the presence in the sample of an absorber having a known concentration. However, in the Jobsis disclosure, the absorber of known concentration is water in tissue. Jobsis states that the variability is about 15%. Thus the concentration of water is subject to the same lack of constancy as in the disclosures by Matcher et al. Jobsis does not discuss the use of any water concentration having a level sufficiently constant to employ as a universal calibration or reference level. In fact, Jobsis states that "the practice of the present invention depends strongly on the development of either a means of translating the results in terms of accepted standards, such as spectrophotometric data in clear solutions, or on the de novo development of an extensive data base where accepted standards are not relevant, i.e., in heterogeneous systems such as the brain."

Pologe (U.S. Pat. No. 5,297,548) discloses the use of simultaneous measurement on a common optical path using pulsatile signals to determine the relative amounts of the dominant absorbers: water, deoxyhemoglobin, and oxyhemoglobin. Pologe does not indicate the possible use of such an apparatus to generate a universal calibration method applicable across multiple subjects. In fact, Pologe indicates that calibration of such an apparatus is intended to be performed empirically.

Other workers, such as Carim et al. (U.S. Pat. No. 5,553,615) and Kuestner (U.S. Pat. No. 5,377, 674), also disclose the use of optical measurements for noninvasive analysis in which one or more detectors are sensitive to wavelengths in which water is the primary absorbing species. However, neither of these disclosures attempts to create a universal calibration or reference level.

As the above discussion suggests, the difficulty of in vivo calibration problem results from a combination of two factors. First, the physical pathlength over which any absorber is present in the tissue or blood is unknown and varies from person-to-person. Second, the intense scattering in tissue and its variation from person-to-person causes the unknown pathlength to be multiplied by an unknown factor that varies with wavelength as well as with subject. A successful solution to this problem requires consideration of both of these issues.

Several patents from the laboratory of the present inventor disclose various procedures which can assist in diminishing some sources of variability and provide better precision. These include U.S. Pat. No. 5,334,287, which describes the basic procedure now known as Kromoscopy, and U.S. Pat. Nos. 5,434,412, 5,424,545, 5,818,048 and 5,672,875, all of which describe improvements and variants on the basic Kromscopic system and methods. The disclosures of all the above-referenced patents are incorporated herein by reference. While many of these patents relate to methods of improving sensitivity and precision of the assays, the biological system is so complex that additional modifications and processes are helpful.

SUMMARY OF THE INVENTION

The method of the present invention makes use of the physiological fact that the kidneys and their associated regulatory systems maintain a virtually constant water concentration in the blood. These regulatory systems maintain the osmotic pressure difference across the filtration systems of the kidney at a stable level and thereby provide the renal system with maximal control over the critical function of solute filtration.

As a result of this regulation, the water concentration in the blood, as measured by a variety of techniques, varies from approximately 830–860 grams per milliliter of blood, a variation of ±1.8% around the average level. In contrast, the concentration of water in tissues can vary by as much as ±20% around the average level. This exceptionally high stability of blood water concentration can be used to calculate concentrations of other constituents in the blood.

In the present invention, this highly stable value for the concentration of water in blood is employed in a universal calibration scheme by combining optical measurements performed at two or more wavelengths in such a way as to eliminate the dependence of concentration on either the thickness of the body part, on the thickness of the absorbing regions within the body part, and on the scattering properties within the body part.

This is accomplished, in a general sense, by employing several types of normalization of the detection channel outputs. For each detection channel the output signals are scaled to fractional modulations by comparing the differential output produced by the cardiac pulse to the background output produced at diastole, as employed in pulse oximetry. In addition, the present invention contemplates additional normalization across multiple detection channels, which normalizes the fractional modulations in each detection channel to the relative amounts of water-specific information included in all the detection channels or in a specific subset of said detection channels. This normalization thereby allows expression of the detection channel responses in such a way that the water-specific information in the resultant data is maintained at a constant level, despite the effects of thickness, of scattering, or of changes in pulse magnitude. The non-water-specific information remaining in the data expressed in this way is then predominantly a function of the relative absorptivities and concentrations of other absorbing constituents in the arterial blood to that of water, and quantitative calibrations and measurements may be performed for such constituents.

In one particularly useful embodiment, readings at two or more channels or detectors containing primarily water-specific information are used separately to provide a means of normalizing the outputs from the other detection channels to achieve concentration measurements. In another embodiment, which is particularly useful when the analyte of interest has only absorption bands that overlap with those of water, the method provides normalization over the totality of the water-specific information available in all of the detection channels. This normalization method is based, in part, on the concept that the response from a series of detectors to a fractional modulation in arterial pulse can be understood and operated upon as a vector in an N dimensional space, where N is the number of simultaneous and spatially congruent detection channels. Each of these vectors can be normalized using a scalar related to the responses of the detector channels to water in vitro. These forms of calibration improve accuracy, including both sensitivity and precision, of the requisite measurements.

In all these embodiments, the initial step in obtaining this combination of measurements is to express each individual optical measurement as the ratio of the difference between the transmission maximum, produced when the arterial blood pressure is at its diastolic minimum level, and the transmission minimum, produced when the arterial blood pressure is at its systolic maximum level. Once the optical measurement has been so scaled to a fractional modulation in each detection channel, the measurements in the various optical channels can be combined in a number of ways, which will be detailed below.

Note that an accurate combination of the fractional modulations across optical channels places a stringent set of requirements on the optical measurements. First, since the condition of the sampled body part varies throughout the cardiac cycle, the measurements must be made before there is any major physical change. For example, since the pulse normally takes about 1 second, taking 25 or more measurements/second will be in short enough time intervals that the physiological changes between measurements are minor. Second, the accuracy of the result of the combination of measurements is maximized when there exists a common light path from the source or sources, through the body part, to each of the several detectors. Third, to produce accurate signal combinations, the effects of scattering on the optical measurements must be minimized by substantially eliminating light reaching the detectors with a large angle of incidence. In a preferred embodiment, light incident on the detectors at an angle greater than about 10 degrees is minimized.

When the above constraints are met, the resulting combination of measurements minimizes adverse effects caused by the concentration of water in the arterial blood, the concentration of the other constituents of the arterial blood, the absorption coefficient of water, and the absorption coefficients of the constituents. This is true because the measurements no longer depend in a substantial manner on the light scattering coefficients within the tissue, on the venous blood component, or on the thickness of the body part.

The present invention provides several alternative configurations for excluding the effect of large-angle radiation from the detectors. In one embodiment, the contribution of scattered radiation to the signal reaching the detector is minimized. The embodiment has been previously disclosed by Block et al. (U.S. Pat. No. 5,672,875) where it is disclosed that restricting the solid angles of illumination and detection substantially eliminates radiation scattered through larger angles reaching the detector(s) relative to that transmitted or scattered though smaller angles. If such apparatus is employed using the data processing means and protocol described above, then the dependence of the combined results upon scattering coefficients will be substantially eliminated.

In a second apparatus configuration, also disclosed in Block U.S. Pat. No. 5,672,875, the contribution of large-angle scattered light reaching the detectors is minimized by generating polarized radiation and allowing said polarized radiation to contact the body part. Radiation scattered through large angles will become depolarized as a consequence of such scattering, and the interposition of an analyzer in the optical path between the body part and the detectors will prevent such depolarized radiation from reaching the detectors. This second configuration may be combined with the use of restricted solid angles of illumination and detection for additional rejection of scattered radiation.

In another configuration, the contribution of radiation scattered at larger angles relative to that scattered at smaller angles or not scattered can be estimated. This estimation is performed by measuring the total radiation reaching sets of detectors with substantially identical spectral response. Each element of each set maintains a common light path with the corresponding element of another set or sets of detectors having a different spectral response characteristic. Then, the combination across spectral responses described above can be carried out on an element-by-element basis. As the geometrical positions of the corresponding elements approach the optical axis of the system, the effect of the larger angle scattered radiation in comparison with that of the directly transmitted radiation will be decreased. Appropriate processing of the multiple element data will then permit a better estimate to be made of the ratio that would be expected in the absence of scattering effects.

The invention provides a method for improving the accuracy of noninvasive, in vivo concentration measurements of a substance of interest in blood. The method has the steps of providing an illumination source that generates illumination radiation to a measurement site across a portion of the spectrum that contains absorbance bands of said substance of interest. The measurement site is illuminated with said illuminating radiation and radiation transmitted or reflected from said measurement site is detected by a detector array. In the preferred embodiment, the detector array has a plurality of detectors having distinct maximum spectral response characteristics in a different region of said portion of the spectrum used for illumination. In one embodiment, the plurality of detectors includes at least a first detector and a second detector having spectral characteristics with greater responsiveness to the absorbance bands of water than to the other constituents in the blood. Each of the detectors in said detector array provides an output signal indicative of the amount of radiation it receives in a selected time period. The method also contains the step of determining a differential value of the output signals for periods of arterial pulse by comparing values obtained during a systolic measurement cycle with values obtained during a diastolic measurement cycle. These differential values are used to generate a series of ratios of the differential output signals generated from the output signals of the non-water detectors to the differential output signals generated from the output signals of each of the water detectors. These ratios provide a means for improving accuracy of the concentration measurements. While this same set of detectors could be used in other embodiments of the invention, it is not practical if one cannot obtain a clear differentiation of the absorption bands. For example, although the absorption bands for hemoglobin, deoxyhemoglobin, and water in the spectral region from 600–1200 nm are separate enough that they can be differentiated and the first method may be used, while for glucose determination, there is too much overlap so a different method is needed. In particular, the scalar normalization is preferred as the overlap of absorption bands increases.

The methods of the invention are useful for both Kromoscopic and non-Kromoscopic (e.g., classic spectrophotometric) measuring systems but have particular advantageous qualities when used with a Kromoscopic system, which meets the conditions of simultaneity and congruence defined above. Optical measurements using detection channels with non-overlapping spectral sensitivities may also employ the methods of this invention, so long as these conditions are substantially met. Accordingly, broadband illuminating radiation or broadband detectors may be used, preferably using detectors with overlapping response. In the alternative, several different illumination sources such as LEDs may be used, with a coded response from a single detector such as is described in U.S. Pat. No. 5,424,545. Similarly, congruent illumination and sampling methods, as well as restricting the solid angle of illumination or detection, using methods such as those described in the afore-mentioned Kromoscopy patents, are useful as part of, and in conjunction with, the methods described herein. The ratios and comparisons required for these methods can be carried out using hardware such as a neural net or software run in a computer or other calculating device. These methods are particularly useful in determining concentration of constituents of blood such as hemoglobin or glucose, in vivo in human patients.

While it is theoretically possible to use the methods disclosed herein with a model system that explains all of the scattering and interferences which effect the present measurements, no such model system is needed. The present methods are equally useful with a chemometric analysis; i.e., an analysis which is not tied to a particular physical representation.

The present invention also provides for a system or apparatus to carry out the disclosed methods. In one embodiment, the apparatus has the two water-responsive channels at its heart, which provides the calibration required to achieve the desired accuracy. If the absorption bands of the analyte of interest have too much overlap with the bands of water, multiple channels which are responsive to both water and the analyte should be utilized, as indicated in the second preferred embodiment. The apparatus may use a single illumination source and a series of detectors, such as in a detector array, or detectors with different filters. Normally, a pulsatile measurement is used, with the apparatus being capable of sufficiently rapid measurements to differentiate and segregate arterial pulse effects. In addition, congruent sampling and/or illumination apparatus, particularly with restricted solid angle, may be used.

By the use of all the components of this invention, simultaneous measurements over a common optical path can be combined with the invariance of the water concentration in blood in such a way as to minimize the effect of the unknown pathlength. Thus, the constant water concentration in arterial blood, the common optical path, and the minimization of the effects of scattered radiation solve the problem of Jobsis (the lack of a translatable standard), while the constant water concentration provides a known, subject-invariant reference to obtain absolute concentrations from the relative concentrations calculated using the procedure disclosed by Pologe.

Thus, an advantage of this invention is that it provides a method for obtaining a universal calibration curve for all patients and under all conditions. This in turn permits the accurate measurement of absolute concentrations of constituents of arterial blood having absorbance in a given spectral sub-region.

Another advantage of this invention is that the method so provided can create a calibration curve for a particular constituent without requiring invasive measurements of that constituent in each subject.

Another advantage of this invention is that the method so provided can reduce measurement variability due to irregularities in cardiac pulse amplitude and the consequent pathlength variation.

Yet another advantage of this method is that it may be employed using a variety of optical configurations and in a variety of spectral sub-regions for noninvasive measurements on any of a variety of body parts, limited only by the requirement that both water and the constituent of interest have measurable absorbance in the spectral sub-region on interest, that the body part permit measurable quantities of radiation to reach the detectors, and that the cardiac pressure produce a measurable change in the radiation reaching the detectors.

Other advantages to the methods resulting from this invention will be apparent from the following detailed description of the invention.

DETAILED DESCRIPTION OF THE INVENTION

Human blood includes a plurality of test constituents present in unknown concentrations together with at least one reference constituent present in a known concentration. Because the concentration of water in blood is both known and nearly invariant across the human population and time, it is convenient to use water as the reference constituent. However, the methods described below can be applied to any constituent which is present at a known concentration.

The method has the steps of providing an illumination source that generates illumination radiation to a measurement site across a portion of the spectrum that contains absorbance bands of said substance of interest. The measurement site is illuminated with said illuminating radiation and radiation transmitted, transflected, or reflected from said measurement site is detected by a detector array. In the preferred embodiment, the detector array has a plurality of detectors having distinct maximum spectral response characteristics in different regions of said portion of the spectrum used for illumination. In one embodiment, the plurality of detectors includes at least a first detector and a second detector having spectral characteristics with greater responsiveness to the absorbance bands of water than to the other constituents in the blood. Each of the detectors in said detector array provides an output signal indicative of the amount of radiation it receives in a selected time period. The method also contains the step of determining a differential value of the output signals for periods of arterial pulsation by comparing values obtained during systolic portions of the arterial pulse with values obtained during a diastolic portions of said pulse.

The method of comparing predominantly water-responsive channels to predominantly non-water-responsive channels is effective if good wavelength separation can be achieved. For example, oxyhemoglobin (and deoxyhemoglobin) are dominate absorbers in the 600–1100 nm range, while water is the dominant absorber in the wavelength range greater than 1100 nm. Accordingly, the ratio method may be used if hemoglobin concentration is sought. However, this is not effective for glucose which has its primary absorbance in the greater than 1100 nm range. Accordingly, another method of using water as a universal standard is needed to eliminate the pathlength variability and other interference problems.

In the case where water is a dominant absorbing constituent in all the detection channels required for measurement of a constituent of interest, then a method is required that represents the constancy of the water concentration of the arterial blood over sets of detection channels employed in the measurement. This representation can be achieved by the consideration of a set of the detection channels as the elements of a vector. The output of N detectors can be used to generate a vector in an N-dimensional space. For example, a vector B can be measured in vivo which represents the set of fractional modulations in each detection channel by the cardiac pulse caused by all the absorbing constituents in the blood. Similarly, a vector G, denoting absorptivity of glucose or any other constituent of interest, may be generated from the in vitro absorptivities of said constituent as measured in each of the N detection channels; each additional absorbing constituent has its own, unique vector. The underlying assumptions in the disclosed method are that the relative magnitude and direction of the vector of the analyte of interest and the vector of water from the detectors in the N-dimensional space will maintain substantially the same relative directions and magnitudes as they have in vitro. Based on these assumptions, an in vitro measurement of water can be taken using the same detector configuration employed for in vivo measurements, and a water vector, w, representing the in vitro water results in the same N-dimensional space, can be determined. By definition, the vector w is deemed to be a unit vector. The dot product of B and w, B·w, is a scalar which can then be used to normalize the vector B. Normalization is achieved by the formula B/B·w yielding a vector $\underline{B}$ which has the same direction as B but with two desirable properties. First, if the only reason for changes in B is variations in pathlength due to changes in blood pressure or other changes in pulse magnitude, the magnitude and direction of $\underline{B}$, computed by this method, will not vary. Second, the component of $\underline{B}$ in the water direction will be the unit vector w; the component of $\underline{B}$ in the water direction is $\underline{B}$·w, resulting in B·w/B·w=1, i.e., the unit vector in the water direction, w. The first property achieves the goal of eliminating dependency on pathlength changes, while the second provides universality of calibration related to the constancy of water content in blood. This self normalization allows information from all the detection channels to be used in the measurement of $\underline{B}$, unlike the prior art reference measurements. One may also use another constituent, G, and perform similar operations as with B to express the response to all the constituents of interest on the same water-normalized scale. Once this has been done, changes in the direction of $\underline{B}$ toward the vector G representing any constituent of interest may be clearly seen to be indicative of increases in the concentration of that constituent. Furthermore, the normalization of all the vectors to the approximately known concentration of water, in the context of the assumption of constant relative directions and magnitudes of all the vectors so normalized, permits the calculation of the magnitude of the concentration change causing such a shift in vector $\underline{B}$.

Figure 1:
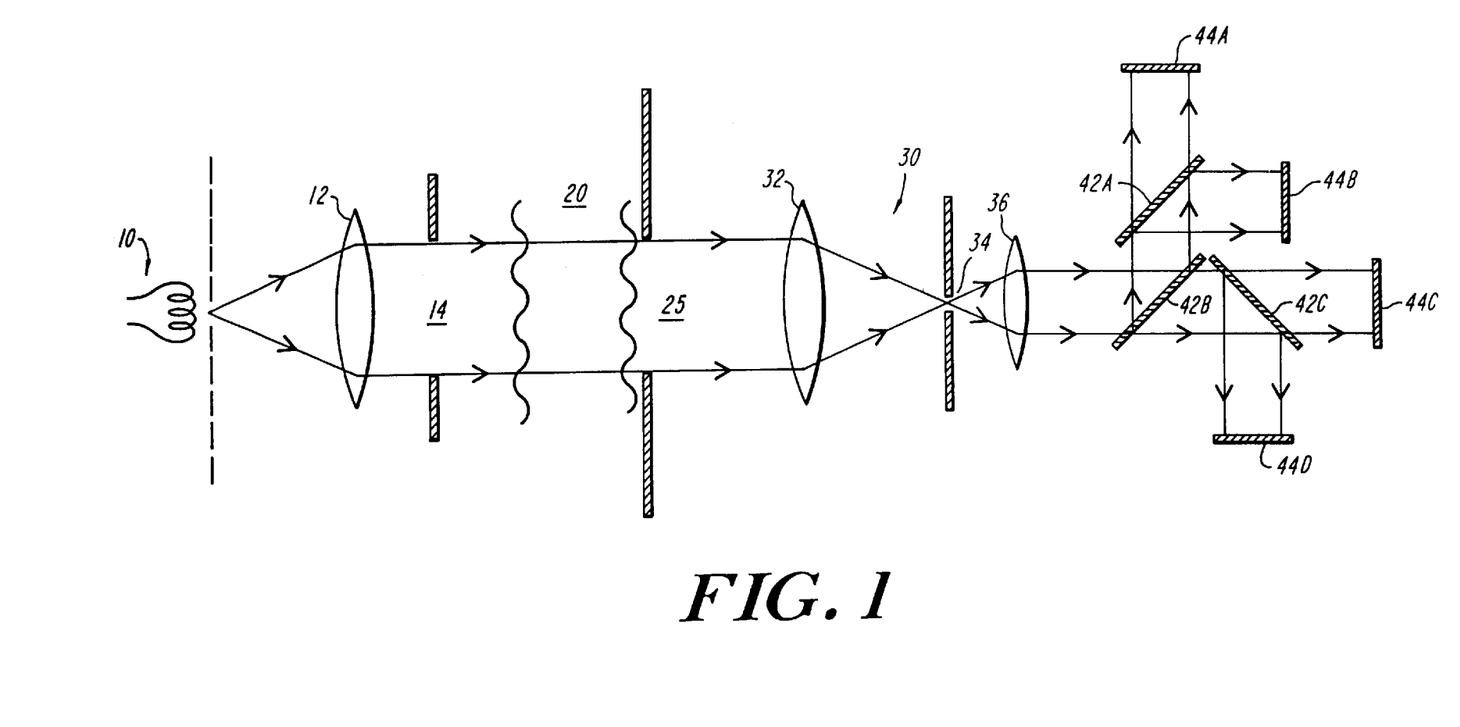
FIG. 1 shows an apparatus for measurement of absorption by blood constituents at a plurality of wavelengths, using a plurality of distinct detectors.

FIG. 1 shows an optical system useful for practicing the present method. This optical system employs collimating optics for both illumination and detection, with the detector having a plurality of detector units placed such that they achieve congruent sampling. Radiation source 10 is selected so that it provides broad spectrum illumination, e.g., 700–2500 nm illumination. Radiation from radiation source 10 passes through collimating lens 12 before striking tissue 20. Optional aperture 14 is shown which helps define the collimation optics in conjunction with collimating lens 12.

Once the radiation has traversed tissue sample 20 and exits the tissue through area defining aperture 25, it passes through detector collimating optics 30 formed of converging lens 32, aperture 34 and recollimating lens 36. This type of collimating optics is conventionally used in telescopes and other devices where collimation of light is desired. The collimated beam exiting collimation optics 30, specifically recollimating lens 36, then goes through a series of beam splitters 42A, 42B and 42C and onto four detector units 44A, 44B, 44C and 44D. The beam splitters and detector units are arranged such that the entire detection unit 40 provides congruent sampling of the beam. More particularly, the beam splitters and detector units are arranged such that the pathlength and angles from recollimating lens 36 to any of detector units 44 are equal and each of detector units 44 are optically superimposable upon the other. If the analyte of interest has spectral characteristics which can be differentiated from those of water, at least two of detector units 44 should have spectral characteristics with greater responsiveness to the absorbance bands of water than to the other constituents of the blood. Although four detector units are shown, the exact number may be varied.

Figure 2A:
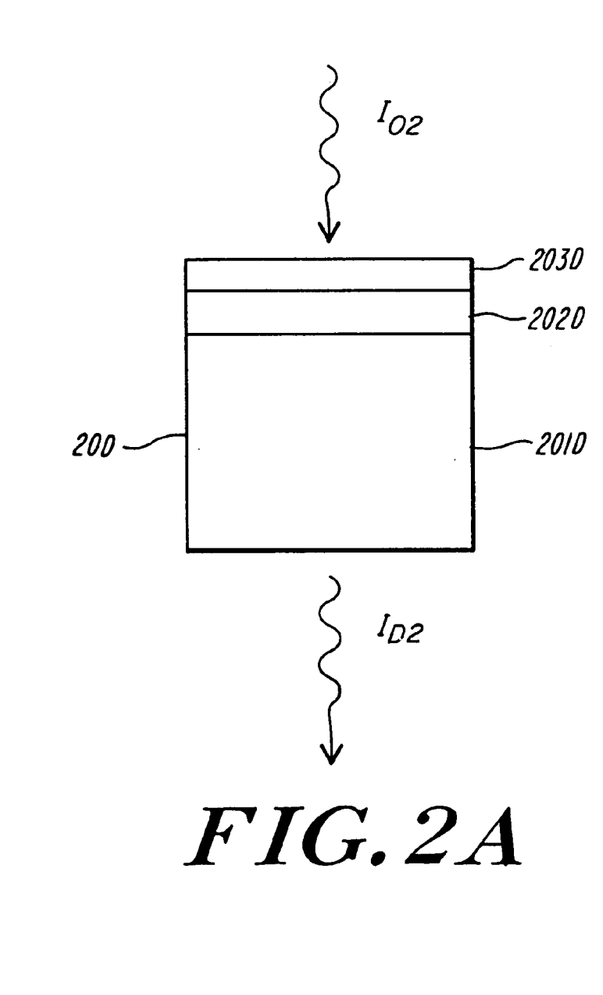
FIG. 2 shows the steps implemented by the processor of FIG. 1 in order to determine absolute concentrations of all constituents in the blood.
Figure 2B:
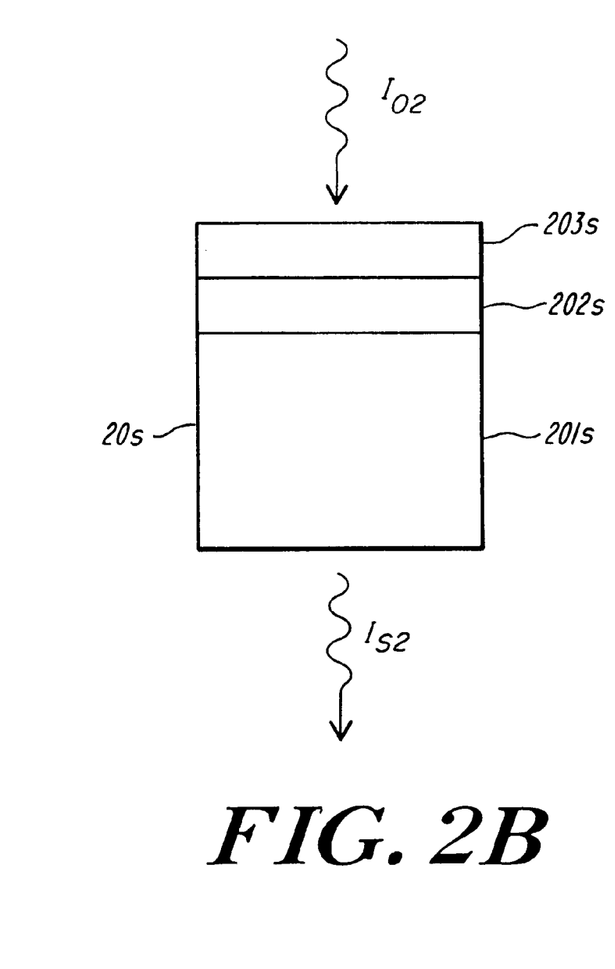

In operation, radiation $I_{o1}$ from the broadband source 10 penetrates the finger 20 where it interacts with the various constituents in the blood and the tissue. As a result of the heartbeat and the resulting pulsatile blood flow, this interaction is a time-varying phenomenon. During the diastolic phase of the heartbeat, as shown in FIG. 2A, the incident radiation interacts with the tissue 201*d*, the venous blood 202*d*, and the arterial blood 203*d* of the finger 20*d*. During the systolic phase, shown in FIG. 2B, the amount of tissue 201*s* and venous blood 202*s* in the finger 20*s* is approximately the same as that which was present in the diastolic phase. However, the amount of arterial blood 203*s* has increased. As a result, the output radiation $I_{S\lambda}$ during the systolic phase differs from the output radiation $I_{D\lambda}$ during the diastolic phase to the extent that the extra blood volume results in additional absorption.

Figure 3:
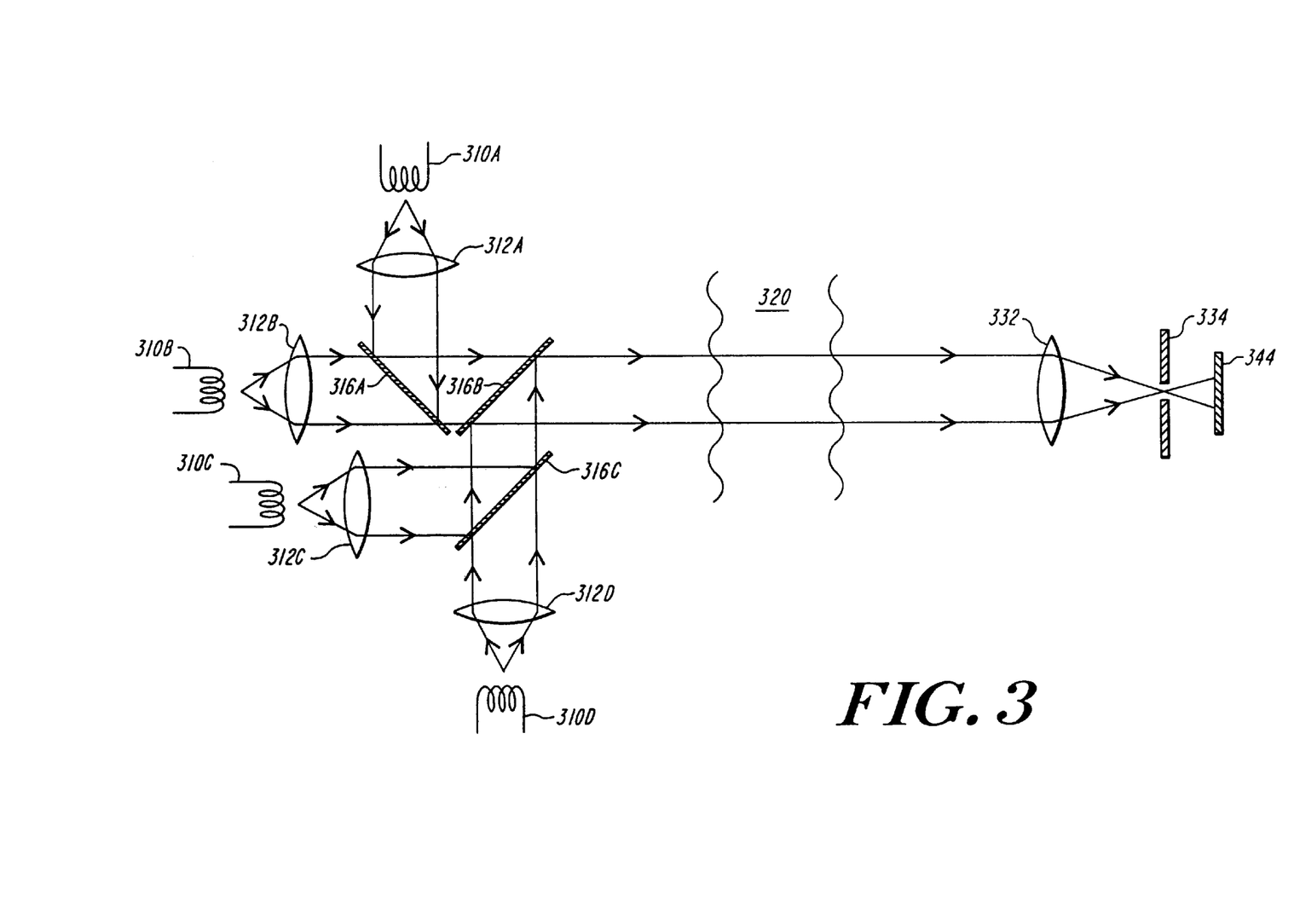
FIG. 3 shows an apparatus for measurement of absorption by blood constituents at a plurality of wavelengths, using a plurality of distinct light sources and a single detector.

FIG. 3 shows a different apparatus for use in practicing the present invention. FIG. 3 shows a system using the beam splitter array of FIG. 1 reversed for congruent illumination rather than congruent sampling. Four radiation sources 310A, 310B, 310C and 310D, are used to illuminate the tissue sample. The radiation issuing from each of the radiation sources goes through a collimating lens (312A, 312B, 312C and 312D, respectively) and then is redirected by one of the beam splitters 316A, 316B or 316C to illuminate tissue 320. The radiation transmitted by tissue 320 passes through converging lens 332 and aperture 334 before striking detector 344. Optionally, an additional lens 336 (not shown) could be used to recollimate the transmitted radiation before it strikes detector 344. The radiation sources, collimating lenses and beam splitters are arranged to provide congruent illumination and each separate radiation source may have an associated modulator to provide a different modulation to the radiation issuing from that radiation source. This type of modulation apparatus, and its advantages, is described in more detail in U.S. Pat. No. 5,424,545. Briefly, using a plurality of modulators, each providing a different modulation to the associated radiation issuing therefrom, and using a form of modulation differentiation at the detector (such as electronically separating the signals based on modulation frequency) provides a method which allows differentiation at the detector of the source of the illuminating radiation, and accordingly allows additional information to be generated from a single detector. For example, if the radiation sources cover different wavelengths, a single detector can differentiate the intensity of the transmitted radiation at each wavelength range by using the modulation to determine the wavelength range. This can eliminate the requirement of the system illustrated above which requires a plurality of detector units. For improved results, both the congruent illumination shown in FIG. 3 and the congruent sampling shown in FIG. 1 may be used in the same device. Similarly, a filter wheel that provides different wavelength transmission can be used on either the illumination or detection side of the device. It is also possible to use fiber optics to transmit light on either the illumination or detector side of the apparatus.

Figure 4:
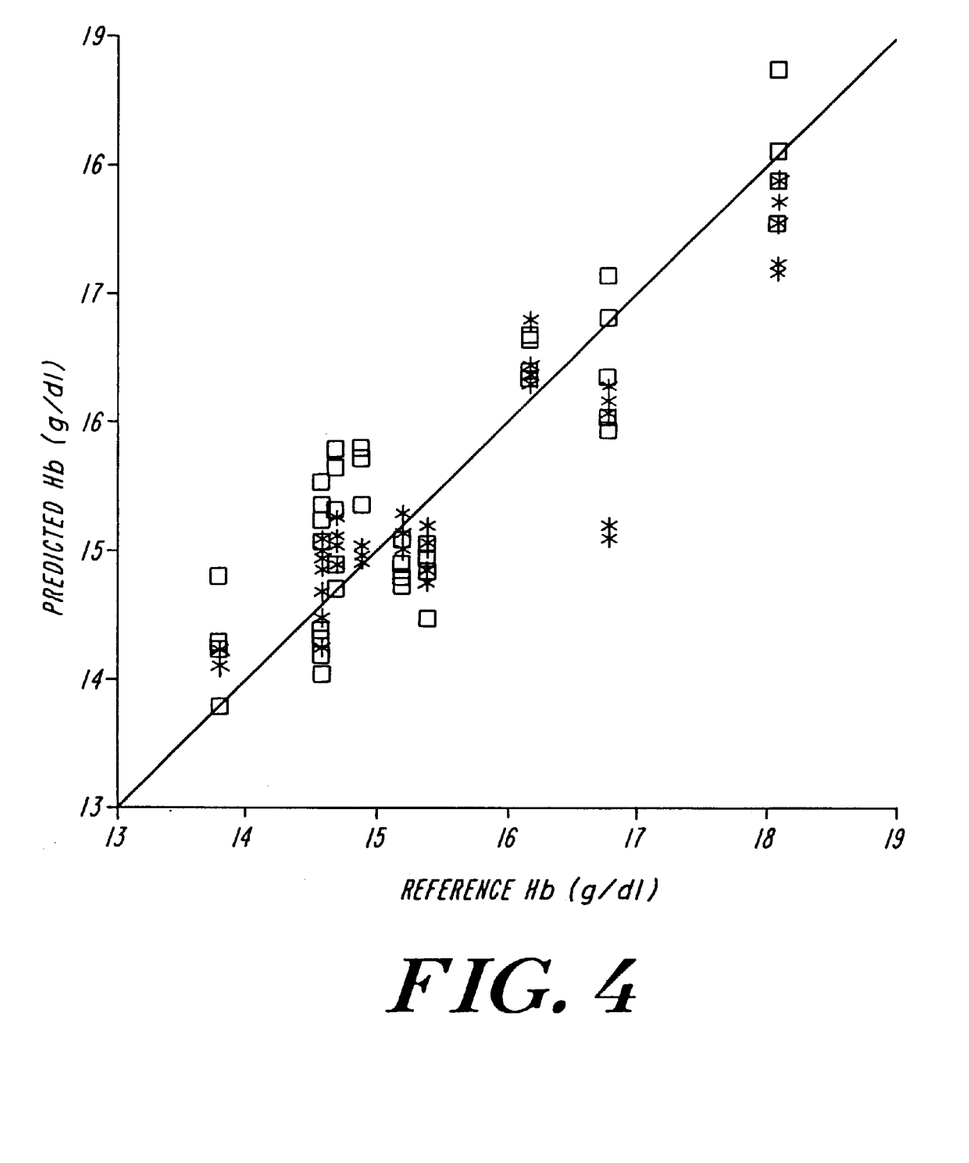
FIG. 4 shows a graph of predicted hemoglobin concentration from a blood sample versus measured hemoglobin using the apparatus of FIG. 1.

FIG. 4 shows a plot of predicted hemoglobin concentration, made using the first embodiment of the in vivo, noninvasive methods and apparatus described herein, with actual hemoglobin as measured using a blood sample. The actual hemoglobin reading is determined using capillary blood sample on a Hemocue B-hemoglobin analyzer (Mission Viejo, Calif.) for 10 samples. The predicted values are determined using an apparatus such as is shown in FIG. 1 in a transmission mode with a fiber optic input placed next to a fingernail and the detector on the opposite side of the finger. Four congruent InGaAs detectors are used, with filters whose maximal transmission is located near 1064 nm, 1200 nm, 1300 nm, and 1625 nm before the individual detectors. The 1200 nm and 1300 nm filters are the water channels. The illumination source is a 2.7 W halogen light source with the fiber optic output focused on elevated fingernails. The elevation of the finger above the heart also appears to improve accuracy. Optical transmission data from each detector channel is digitized by HP3458A multimeters and transmitted to a Pentium PC via Labview software for post-processing to derive pulsatile modulation values by Matlab software.

Each data run consists of thirty seconds of raw data, or about 30 cardiac pulses at normal cardiac rates. The data from each run was used in a ratio calculation, with all four possible hemoglobin to water detection channel ratios being used to generate the results. The linear regression analysis is shown in FIG. 4. The standard error of calibration was 0.24 g Hb/dl, on values ranging from 13–19 g Hb/dl.

The advantages of the present invention apply to spectrophotometric systems such as those employed in pulse oximetry. While the shot-noise constraints on the detected intensity are lower because the absorption of the hemoglobins are so much larger the acceptance angle restrictions provide greater linearity and improved calibratability, as well as reduction in the severity of motion and breathing artifacts, and other limitations on universality of calibration.

For the analysis of trace constituents where the high photon flux requirement is critical, the present invention is particularly advantageous when combined with the use of broadband and broadband overlapping detectors, as taught in the Block '265 Patent and the parent applications.

The foregoing description is meant to be explanatory only and is not intended to be limiting as to the scope of the invention. The invention is defined by the following claims.

What is claimed is:

1. A method of improving accuracy in non-invasive, in vivo concentration measurements of a substance of interest in blood comprising the steps of:

providing an illumination source which is adapted to generate illumination radiation to a measurement site, said illumination source providing illumination radiation across a portion of the spectrum which contains absorbance bands of said substance of interest;

illuminating said measurement site with said illumination radiation;

detecting radiation transmitted, transflected, or reflected from said measurement site with a detector array, said detector array having a plurality of detectors each having broadband spectral response characteristics with broadband spectral response characteristics with distinct maximum spectral response characteristics within different regions of said portion of the spectrum used for illuminating; each of said detectors in said detector array being selected and located such that said detector collects radiation only from a limited solid angle, said detector array providing an output signal indicative of the amount of radiation it receives in a selected time period;

determining a differential value of said output signals for periods of arterial pulsations of the blood in said measurement site, said differential values being a comparison of values obtained during a systolic portion of said pulsations and values obtained during a diastolic portion of said pulsations; and generating a response which comprises a comparison of said differential value of said output signals to a simultaneous water-specific measurement, said water specific measurement being related to the amount of water in said blood during the measurement cycle, said water specific measurement being generated using at least a portion of said detector array;

whereby said response provides a means for improving the accuracy of said concentration measurements.

2. The method of claim 1 wherein said plurality of detectors includes at least a first detector and a second detector having spectral characteristics with greater responsiveness to absorbance bands of water than to other constituents in said blood, and whereby said comparison step comprises comparing a series of ratios of the differential value of the output signals generated from the output signals of non-water detectors to the differential value of the output signals generated from the output signals of water detectors.

3. The method of claim 1 wherein said comparison step is carried out utilizing a computing device.

4. The method of claim 1 wherein said comparison step is carried out utilizing a neural network.

5. The method of claim 1 wherein said method of improving accuracy further comprises the steps of taking in vitro measurements of water absorbance using said detector array, projecting vectors corresponding to the differential value of the output signals for the arterial pulsation from the in vivo measurements and the in vitro water measurements in the same N-dimensional space, said N-dimensional space comprising a dimension for the response of each detector in said detector array, generating a scalar corresponding to the magnitude of the projection of the differential value of the output signal vector onto the water vector, and normalizing the differential value of the output signals for the arterial pulsation utilizing said scalar.

6. A system for noninvasive in vivo measurements of concentration of a substance of interest in blood comprising:

an illumination source which generates illumination radiation to a measurement site, said illumination source providing illumination across a portion of the spectrum which contains absorbance bands for said substance of interest;

a detector array for detecting radiation transmitted, transflected, or reflected from said measurement site, said detector array having a plurality of detectors each having broadband spectral response characteristics with distinct maximum spectral response characteristics within different regions of said portion of the spectrum used for illumination; each of said detectors in said detector array being selected and located such that said detector collects radiation only from a limited solid angle, said detector array providing an output signal indicative of the amount of radiation it receives in a selected time period;

means for determining a differential value of said output signals for periods of arterial pulsations of the blood in said measurement site, said differential values being a comparison of values during a systolic portion of said pulsations and values during a diastolic portion of said pulsations; and means for generating a response which comprises a comparison of said differential output signals to a simultaneous water-specific measurement, said water specific measurement being related to the amount of water in said blood during the measurement cycle and said water specific measurement being generated using at least a portion of said detector array.

7. The system of claim 6 wherein said plurality of detectors includes at least a first detector and a second detector having spectral characteristics with greater responsiveness to absorbance bands of water than to other constituents in said blood, in which said comparison comprises means for generating series of ratios of the differential value of the output signals generated from the output signals of non-water detectors to the differential value of the output signals generated from the output signals from each water detector.

8. The system of claim 6 wherein said illumination source is arranged to provide congruent illumination.

9. The system of claim 6 wherein said detector array is arranged to provide congruent detection.

10. A method of reducing measurement variability due to irregularities in cardiac pulse amplitude and the consequent pathlength variation in noninvasive, in vivo concentration measurements of a substance of interest in blood comprising the steps of:

providing an illumination source which is adapted to generate illumination radiation to a measurement site, said illumination source providing illumination radiation across a portion of the spectrum which contains absorbance bands of said substance of interest;

illuminating said measurement site with said illumination radiation;

detecting radiation transmitted, transflected, or reflected from said measurement site with a detector array, said detector array having a plurality of detectors each having broadband spectral response characteristics with distinct maximum spectral response characteristics within different regions of said portion of the spectrum used for illuminating; each of said detectors in said detector array being selected and located such that said detector collects radiation only from a limited solid angle, said detection array providing an output signal indicative of the amount of radiation it receives in a selected time period;

determining a differential value of said output signals for periods of arterial pulsations of the blood in said measurement site, said differential values being a comparison of values obtained during a systolic portion of said pulsations and values obtained during a diastolic portion of said pulsations; and generating a response which comprises a comparison of said different value of the value of said output signals to a simultaneous water-specific measurement, said water specific measurement being related to the amount of water in blood during a measurement cycle, said water-specific measurement being generated using at least a portion of said detector array;

whereby said response provides a means for reducing measurement variability due to irregularities in cardiac pulse amplitude and the consequent pathlength variation in said concentration measurements.

11. The method of claim 10 wherein said plurality of detectors includes at least a first detector and a second detector having spectral characteristics with greater responsiveness to absorbance bands of water than to other constituents in said blood, and whereby said comparison step comprises comparing a series of ratios of the differential value of the output signals generated from the output signals of non-water detectors to the differential value of the output signals generated from the output signals of water detectors.

12. The method of claim 10 wherein said method of reducing measurement variability due to irregularities in cardiac pulse amplitude and the consequent pathlength variation further comprises the steps of taking in vitro measurements of water absorbance using said detector array, projecting vectors corresponding to the differential value of the output signals for the arterial pulsation from the in vivo measurements and the in vitro water measurements in the same N-dimensional space, said N-dimensional space comprising a dimension for the response of each detector in said detector array, generating a scalar corresponding to the magnitude of the projection of the differential value of the output signal vector onto the water vector, and normalizing the differential value of the output signals for the arterial pulsation utilizing said scalar.

* * * * *